United States Patent
Kostrzewski

(10) Patent No.: US 11,344,298 B2
(45) Date of Patent: May 31, 2022

(54) SURGICAL STAPLING DEVICE

(71) Applicant: Covidien LP, Mansfield, MA (US)

(72) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 151 days.

(21) Appl. No.: 16/705,471

(22) Filed: Dec. 6, 2019

(65) Prior Publication Data

US 2021/0169474 A1    Jun. 10, 2021

(51) Int. Cl.
*A61B 17/068* (2006.01)
*A61B 17/072* (2006.01)

(52) U.S. Cl.
CPC .... *A61B 17/0684* (2013.01); *A61B 17/07207* (2013.01); *A61B 2017/07271* (2013.01); *A61B 2560/0443* (2013.01)

(58) Field of Classification Search
CPC .................. A61B 17/0684; A61B 17/1155
See application file for complete search history.

(56) References Cited

U.S. PATENT DOCUMENTS

| | | | |
|---|---|---|---|
| 6,202,914 B1 | 3/2001 | Geiste et al. | |
| 9,055,943 B2 | 6/2015 | Zemlok et al. | |
| 2009/0182354 A1* | 7/2009 | Blier | A61B 17/04 606/148 |
| 2013/0098965 A1 | 4/2013 | Kostrzewski et al. | |
| 2013/0200130 A1 | 8/2013 | Wenchell et al. | |
| 2016/0006406 A1 | 1/2016 | Villemoes | |
| 2016/0192927 A1* | 7/2016 | Kostrzewski | A61B 17/07207 606/219 |

* cited by examiner

*Primary Examiner* — Nathaniel C Chukwurah
(74) *Attorney, Agent, or Firm* — Carter, DeLuca & Farrell LLP

(57) ABSTRACT

A surgical stapling device includes an elongate member and a loading unit. The loading unit includes a tool portion and a body portion including a first portion having a first length, a second portion having a second length, and a third portion having a third length. The first portion is configured to be releasably secured with the elongate member. The second portion is distal of the first portion and dimensioned to be received in the elongate member. The third portion is distal of the second portion. At least the second or third portion is configured to engage the elongate member in a sealing relation. The second length is greater than the first and third lengths. The third portion of the body portion is dimensioned to be flush with the elongate member when the first and second portions are received in the elongate member.

19 Claims, 8 Drawing Sheets

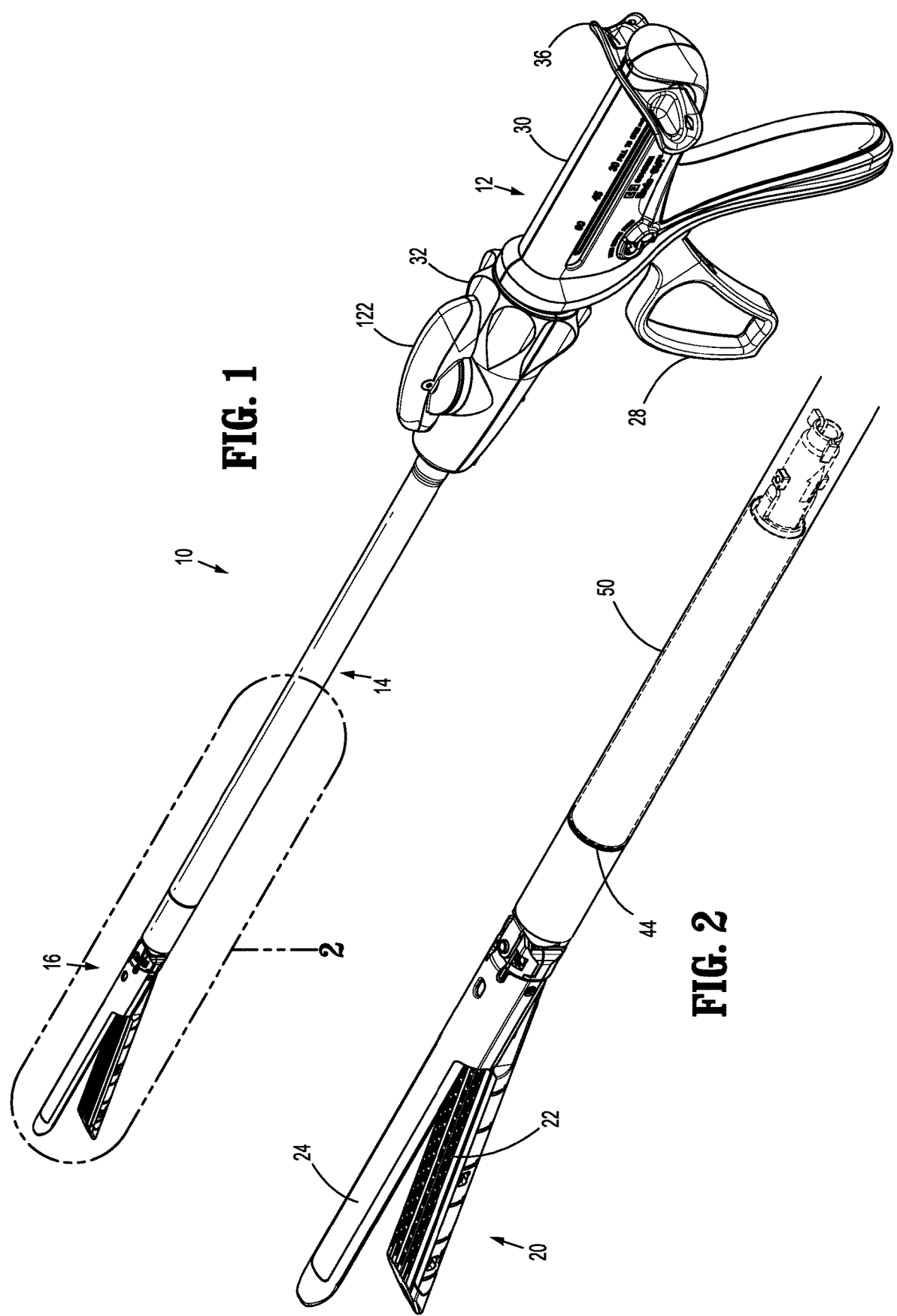

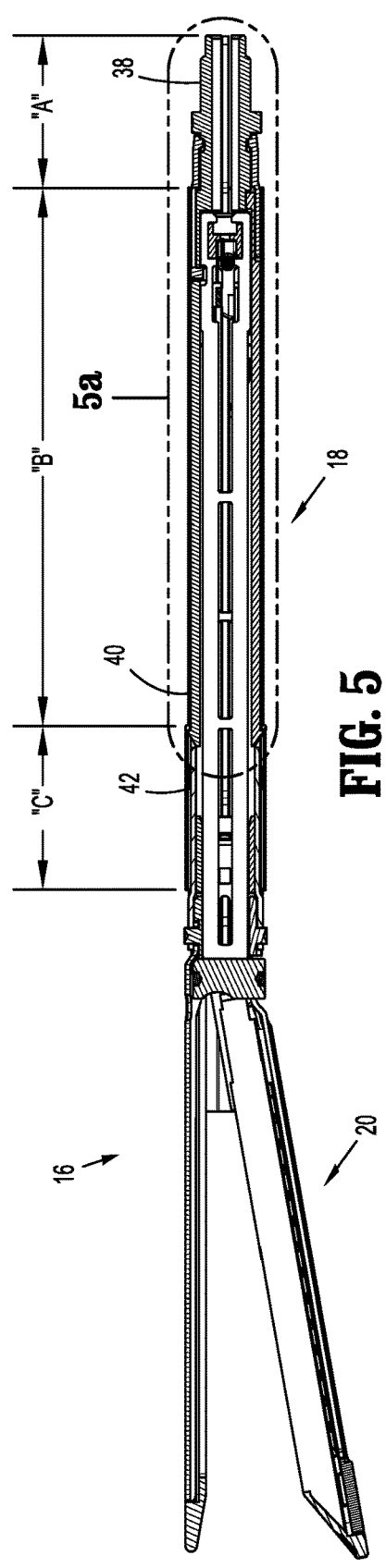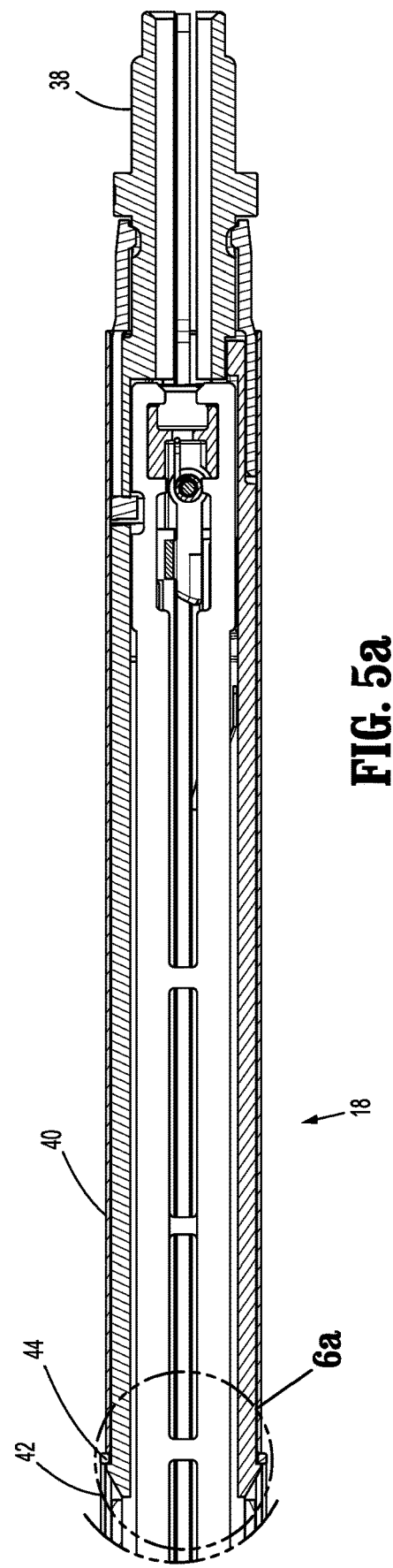
FIG. 5
FIG. 5a

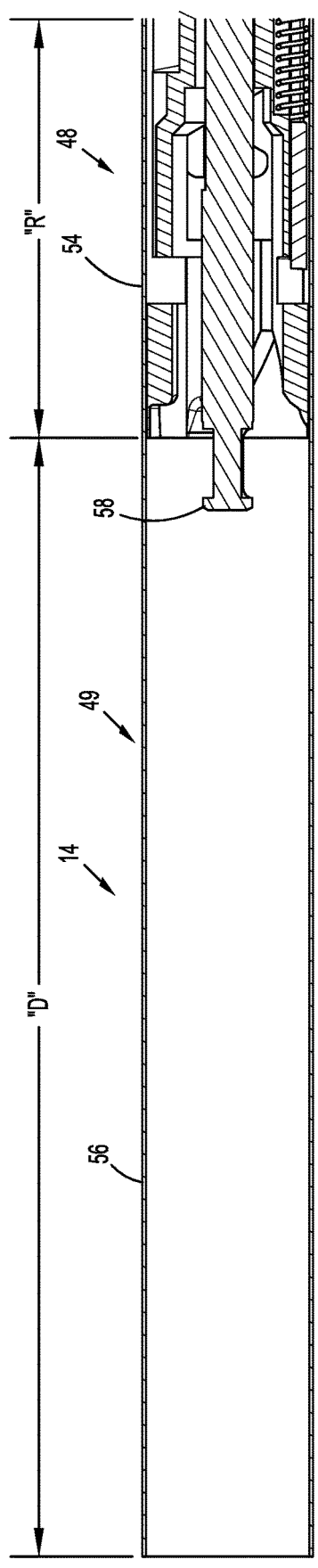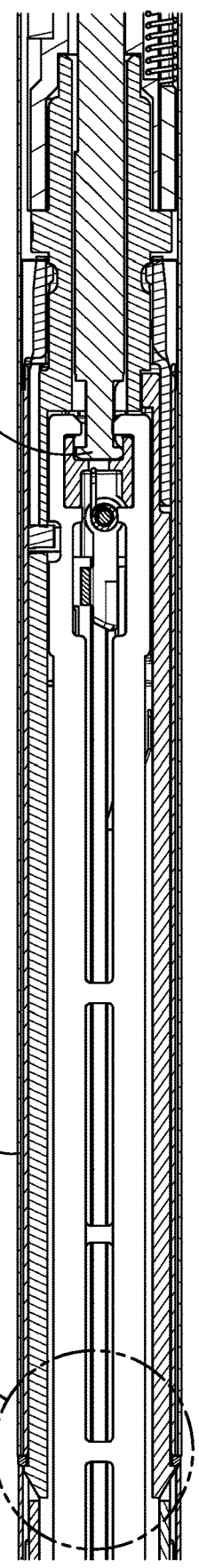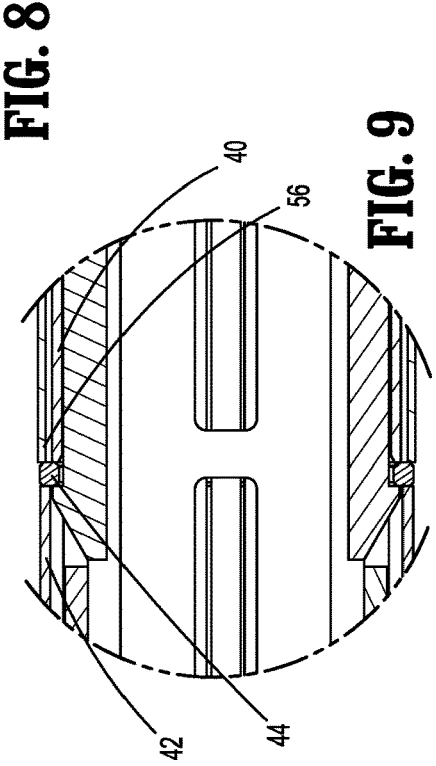
FIG. 7
FIG. 8
FIG. 9

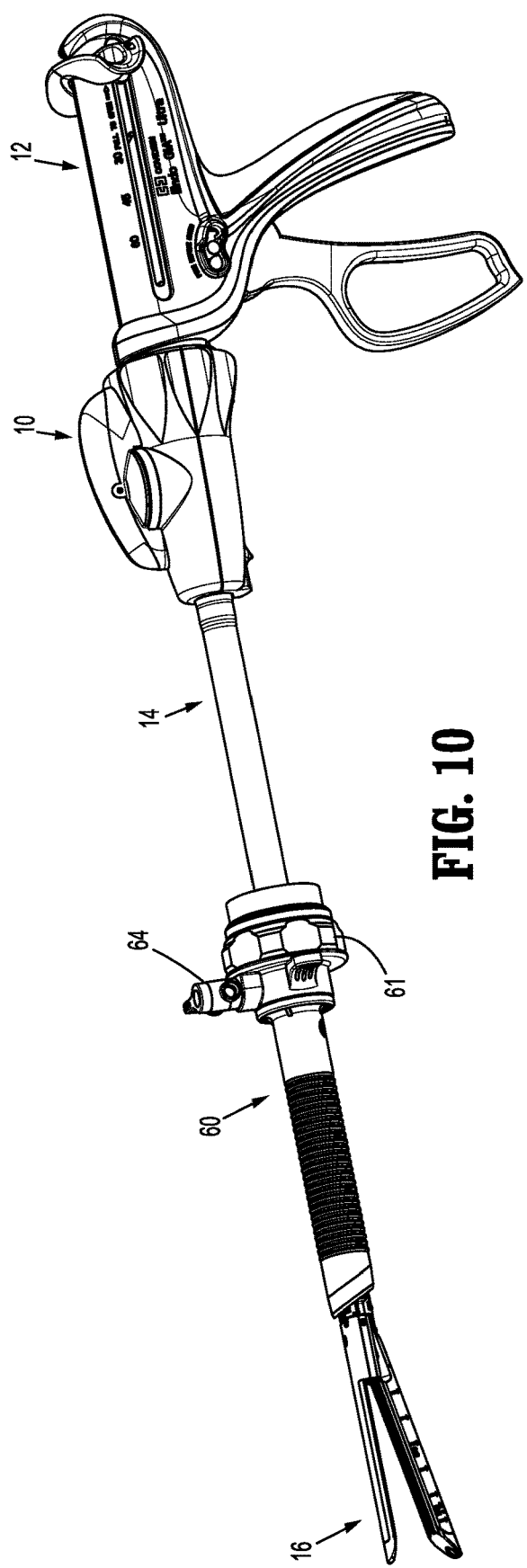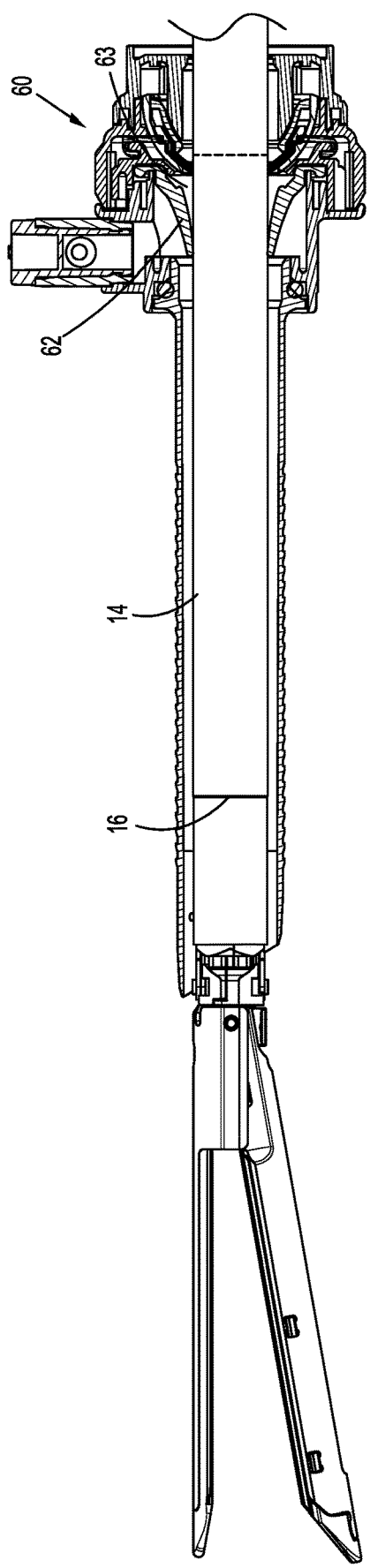

SURGICAL STAPLING DEVICE

BACKGROUND

Technical Field

The present disclosure relates to surgical stapling devices and, more particularly, to a surgical stapling device including a loading unit that provides a stable connection with an elongate member of the surgical stapling device.

Background

Surgical stapling devices are commonly used during a variety of surgical procedures to staple and/or cut tissue. Stapling and cutting of tissue can be accomplished more quickly using surgical stapling devices than can be accomplished using traditional suturing techniques. In addition, endoscopic stapling devices can be used to perform less invasive surgical procedures than possible using traditional suturing techniques. As such, surgical stapling devices as compared to traditional suturing techniques reduce patient trauma and patient recovery times and are desirable.

Typically, linear endoscopic surgical stapling devices include a tool assembly having an anvil assembly and a staple cartridge that are movable in relation to each other between open and clamped positions. The staple cartridge defines a plurality of staple pockets that receive staples and the anvil assembly defines a plurality of staple deforming pockets. When the tool assembly is in the clamped position, the staple deforming pockets of the anvil assembly are aligned with the staple pockets of the cartridge assembly such that legs of the staples are received and deformed within the staple deforming pockets when the stapling device is fired. The staple cartridge and the anvil assembly must be properly aligned to effect proper formation of the staple legs.

Due to the small dimensions of a tool assembly of an endoscopic surgical stapling device, the endoscopic surgical stapling device may have limited rigidity. This limited rigidity makes it difficult to stabilize the tool assembly on a distal portion of an elongate shaft of a surgical stapling device. Therefore, a need exists for a simple and effective endoscopic surgical stapling device that provides adequate rigidity to meet the needs of surgical procedures, while enabling easy and efficient attachment and removal of the tool assembly from the surgical stapling device.

SUMMARY

In accordance with an embodiment of the present disclosure, a surgical stapling device includes an elongate member and a loading unit. The elongate member defines a lumen therethrough. The loading unit is releasably attachable to the elongate member. The loading unit includes a tool portion and a body portion configured to be releasably coupled to the elongate member. The body portion includes a first portion having a first length, a second portion having a second length, and a third portion having a third length. The first portion is configured to be releasably secured with the elongate member. The second portion is distal of the first portion and dimensioned to be received in the elongate member. The third portion is distal of the second portion. At least the second or third portion is configured to engage the elongate member in a sealing relation. The second length is greater than the first and third lengths. The third portion of the body portion is dimensioned to be flush with the elongate member when the first and second portions are received in the elongate member.

In an embodiment, the second length of the second portion may be greater than the sum of the first and third lengths of the first and third portions.

In another embodiment, the second portion of the body portion may be dimensioned to provide a frictional contact with the elongate member.

In yet another embodiment, the second portion of the body portion may have a second diameter and the third portion has a third diameter larger than the second diameter.

In still yet another embodiment, the second portion of the body portion may have a uniform diameter.

In an embodiment, the body portion may further include a seal member disposed about the second portion.

In another embodiment, the seal member may be disposed adjacent the third portion.

In yet another embodiment, the seal member may be flush with the third portion.

In still yet another embodiment, the seal member may have a diameter larger than a diameter of the third portion.

In still yet another embodiment, the seal member may be formed of elastic or compressible material to form a fluid-tight seal against an inner surface of the elongate member.

In an embodiment, the elongate member may have a uniform diameter.

In another embodiment, the tool portion may include an anvil assembly and a cartridge assembly.

In accordance with another embodiment of the present disclosure, a surgical kit includes a surgical stapling device and an access port. The surgical stapling device includes an elongate member and a loading unit releasably attachable to the elongate member. The elongate member defines a lumen therethrough. The loading unit includes a tool portion including an anvil assembly and a cartridge assembly, and a body portion configured to be releasably coupled to the elongate member. The body portion includes a first portion having a first length, a second portion having a second length, a third portion having a third length. The first portion is configured to be releasably secured with the elongate member. The second portion is distal of the first portion. The second portion is dimensioned to be received in the elongate member. The second portion includes a seal member configured to provide a fluid-tight seal against the elongate member. The third portion is distal of the second portion. The third portion is configured to engage the elongate member in a sealing relation. The access port includes a housing and a tubular member extending from the housing. The housing includes a lumen dimensioned to receive the loading unit and the elongate member of the surgical stapling device. The housing includes a fluid port and a seal disposed in the lumen to provide a fluid-tight seal against an object inserted therethrough. The second portion of the body portion of the surgical stapling device is disposed distal of the seal of the access port when the elongate member and the loading unit are received through the access port.

BRIEF DESCRIPTION OF THE DRAWINGS

Various embodiments of the presently disclosed surgical stapling device are described herein with reference to the drawings:

FIG. 1 is a perspective view of a surgical stapling device in accordance with an embodiment of the present disclosure;

FIG. 2 is a perspective view of a loading unit and a distal portion of an elongate member of the surgical stapling device of FIG. 1, illustrating a proximal portion of the loading unit in phantom positioned within the elongate member of the surgical stapling device;

FIG. 5 is a side cross-sectional view of the loading unit of FIG. 1;

FIG. 5a is an enlarged view of the indicated area of detail of FIG. 5;

FIG. 6a is an enlarged view of the indicated area of detail of FIG. 5a;

FIG. 7 is a partial cross-sectional view of the elongate member of the surgical stapling device of FIG. 3;

FIG. 8 is a cross-sectional view of a distal portion of the elongate member and the loading unit of FIG. 1;

FIG. 9 is an enlarged view of the indicated area of detail of FIG. 8;

FIG. 10 is a side perspective view of the surgical stapling device of FIG. 1 extending through an access port;

FIG. 10a is a cross-sectional view of the loading unit of the surgical stapling device of FIG. 10 and the access port.

DETAILED DESCRIPTION

Figure 3:
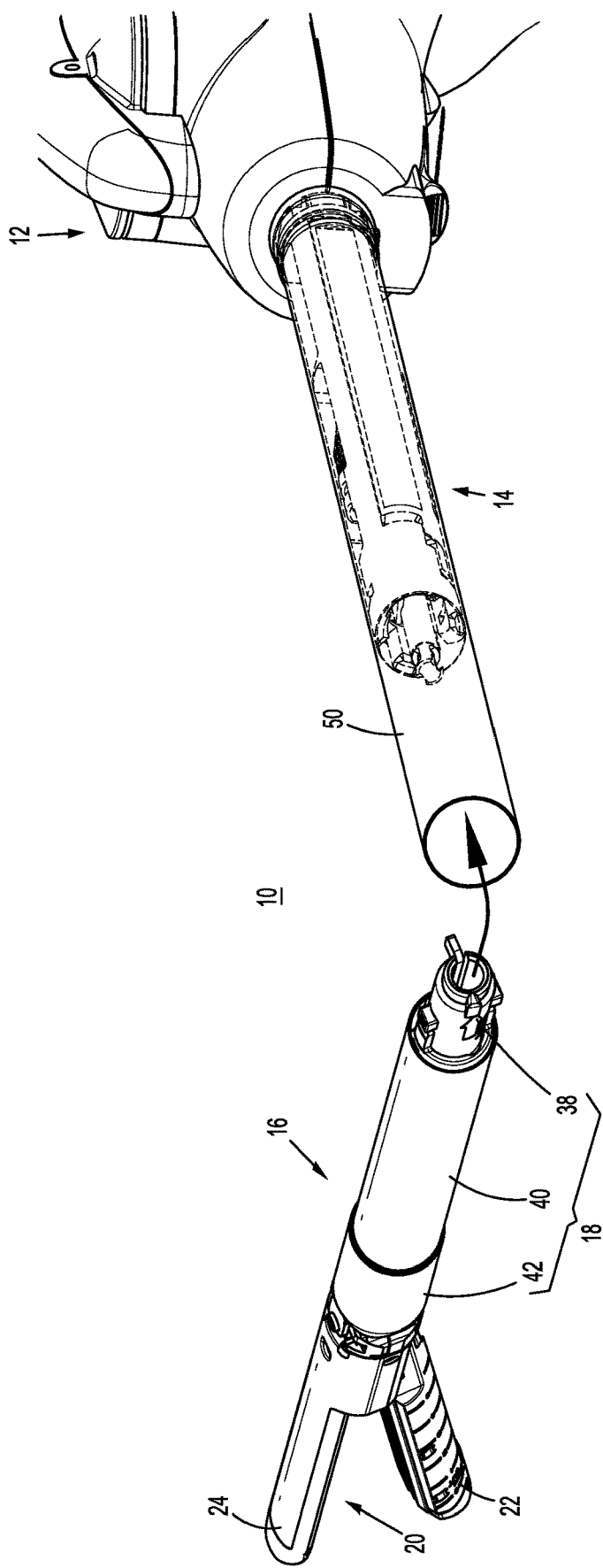
FIG. 3 is a perspective view of the surgical stapling device of FIG. 1 with the loading unit detached from the elongate member and internals of the elongate member shown in phantom.

The presently disclosed surgical stapling device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

With reference to FIGS. 1 and 2, a surgical stapling device in accordance with an embodiment of the present disclosure is generally shown as a surgical stapling device 10. The surgical stapling device 10 includes a handle assembly 12, an elongate member 14 extending from the handle assembly 12, and a loading unit 16 that is releasably secured to the elongate member 14. The elongate member 14 includes a tubular portion 56 (FIG. 7) that is described in further detail below.

The handle assembly 12 includes a barrel portion 30 pivotably supporting an actuation trigger 28. The barrel portion 30 further includes a rotatable member 32 that is operatively coupled to the elongate member 14 for concomitant rotation therewith. The handle assembly 12 further includes an articulation lever 122 that is configured to effect articulation of the tool assembly 20, and a knob 36 that is movably supported on the barrel portion 30 to effect transition of the surgical stapling device 10 from an advanced position to a retracted position.

Figure 4:
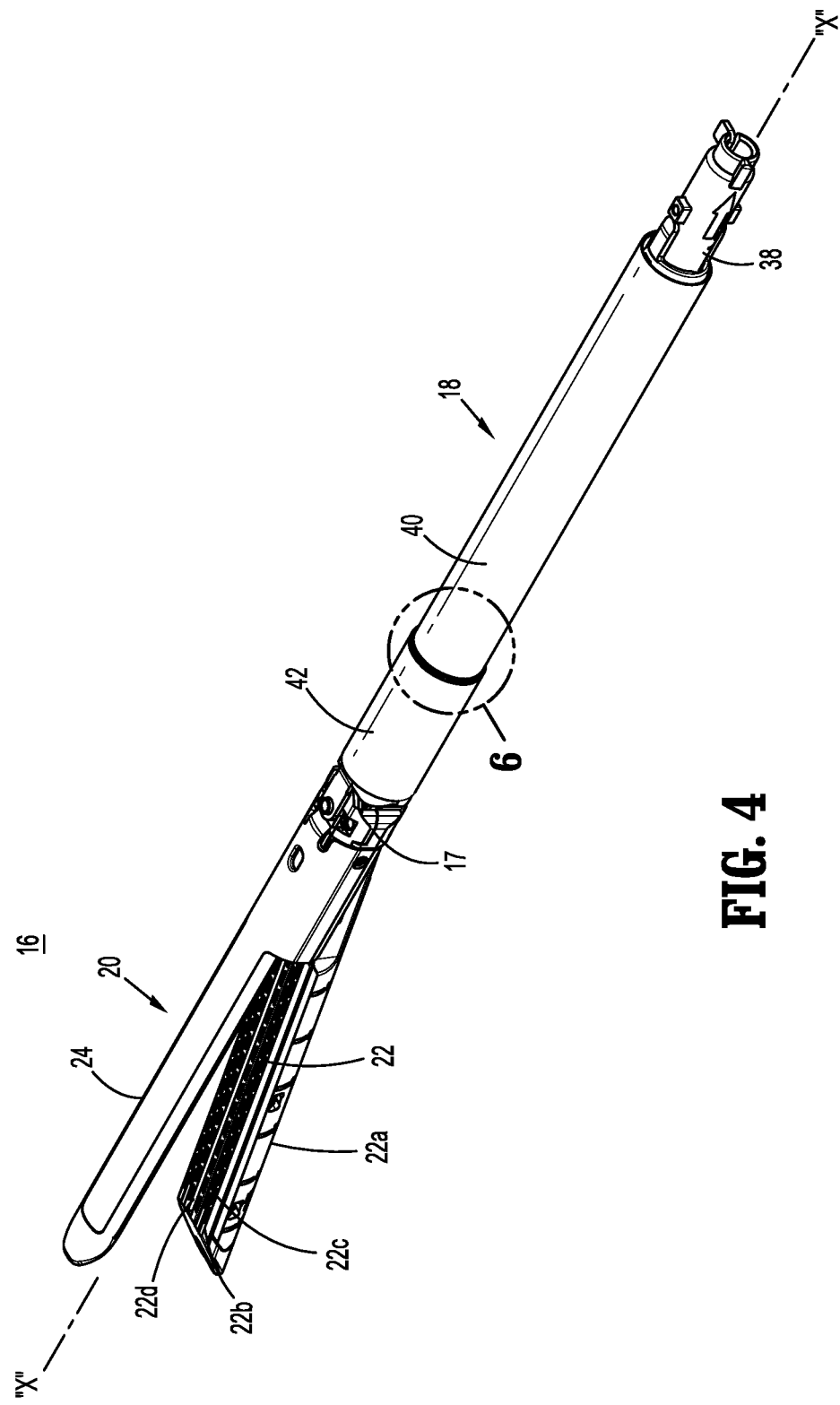
FIG. 4 is a side perspective view of the loading unit of FIG. 1.

With reference to FIGS. 3 and 4, the loading unit 16 includes a tool assembly 20 and a body portion 18. The tool assembly 20 includes a cartridge assembly 22 and an anvil assembly 24. The cartridge assembly 22 is movable in relation to the anvil assembly 24 between open and approximated positions. A mounting assembly 17 is provided to couple the tool assembly 20 to the body portion 18 to facilitate pivotal movement of the tool assembly 20 about an axis transverse to a longitudinal axis "X-X" of the body portion 18. The body portion 18 includes a proximal portion that is configured to be releasably coupled to the elongate member 14.

The anvil assembly 24 includes a tissue contacting surface (not shown) that defines linear rows of staple forming depressions (not shown). The anvil assembly 24 may also define a longitudinal slot configured to receive a knife blade (not shown) to facilitate longitudinal movement of the knife blade through the tool assembly 20. The cartridge assembly 22 includes a cartridge body 22a and a staple cartridge 22b that may be removably received in the cartridge body 22a to facilitate replacement of a spent staple cartridge 22b. The staple cartridge 22b includes a plurality of staples (not shown) and a tissue contacting surface 22c that is configured to receive support tissue. The tissue contacting surface 22 defines staple retention slots that receive staples (not shown) and a knife channel 22d that receives the knife blade to facilitate longitudinal movement of the knife blade through the tool assembly 20.

Reference may be made to U.S. Patent Application Publication Nos. 2013/0098965 and 2013/0200130, the entire contents of each of which is incorporated herein by reference, for a detailed discussion of the construction and operation of an exemplary manually powered surgical stapling device for driving the tool assembly 20. Alternatively, the surgical stapling device 10 may include a powered electromechanical handle assembly to drive the tool assembly 20. Reference may also be made to U.S. Pat. No. 9,055,943 and U.S. Patent Application Publication No. 2016/006406, the entire contents of each of which is incorporated herein by reference, for a detailed discussion of the construction and operation of exemplary powered handle and adapter assemblies.

With reference now to FIGS. 4-5a, the body portion 18 of the loading unit 16 includes a first portion 38 having a first length "A" (FIG. 5), a second portion 40 having a second length "B" (FIG. 5), and a third portion 42 having a third length "C" (FIG. 5). The first portion 38 is configured to be releasably secured with the elongate member 14 of the surgical stapling device 10. The second portion 40 is dimensioned to be received within the tubular member 56 (FIG. 7) of the elongate member 14 such that the elongate member 14 extends over the first and second portions 38, 40 of the body portion 18 of the loading unit 16. The tubular member 56 increases the rigidity of a proximal portion of the loading unit 16 and the rigidity of the interconnection of the loading unit 16 and the elongate member 14 to improve the stability of tool assembly 20 of the surgical stapling device 10.

The third portion 42 of the loading unit 16 may be dimensioned to be flush with the tubular member 56 of the elongate member 14 when the elongate member 14 is positioned over the first and second portions 38, 40 of the loading unit 16. In order to further enhance structural rigidity of the loading unit 16 when the loading unit 16 is operatively coupled with the elongate member 14, the second portion 40 of the loading unit 16 may be dimensioned to comprise a substantial portion of the overall length of the body portion 18 of the loading unit 16. For example, the second length "B" of the second portion 40 may be greater than the sum of the first and third lengths "A", "C" of the first and third portions 38, 42. Such a configuration stabilizes the position of the tool assembly 20 in relation to the elongate member 14 during operation of the surgical stapling device 10 to improve a clinician's control of placement of the tool assembly 20 in relation to target tissue to be treated.

In addition, the second portion 40 may have a diameter dimensioned to provide a friction fit with the elongate member 14 to further enhance securement of the loading unit 16 with the elongate member 14 and stabilize the position of the tool assembly 20. The second portion 40 may have a diameter larger than a diameter of the first portion 38, or a diameter that is uniform. It is also contemplated that the second portion 40 of the loading unit 16 may be tapered along the second length "B" in order to increase the frictional forces between the loading unit and the tubular member 56 of the elongate member 14 as the loading unit 16 is inserted into the elongate member 14. In some embodiments, the second portion 40 may have a second diameter, and the third portion 42 may have a third diameter that is larger than the second diameter such that the second and third portions 40, 42 provide stepped configuration.

Figure 6:
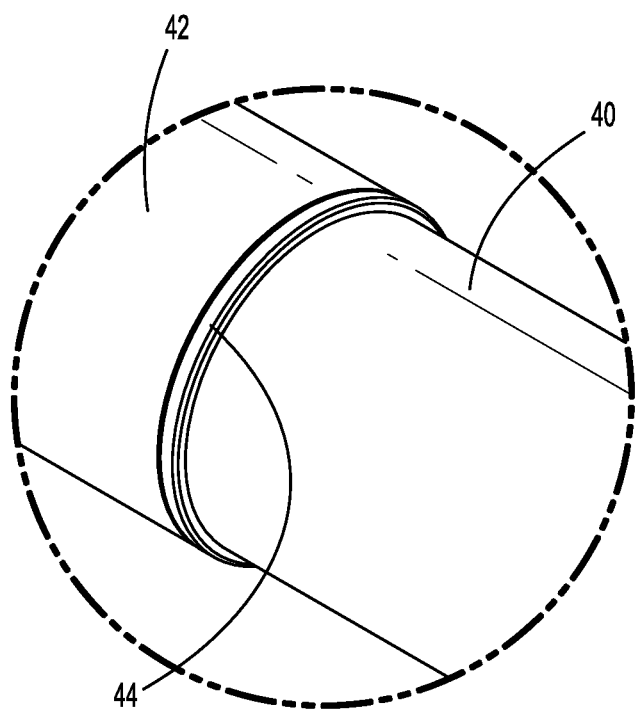
FIG. 6 is an enlarged view of the indicated area of detail of FIG. 4.
Figure 6A:
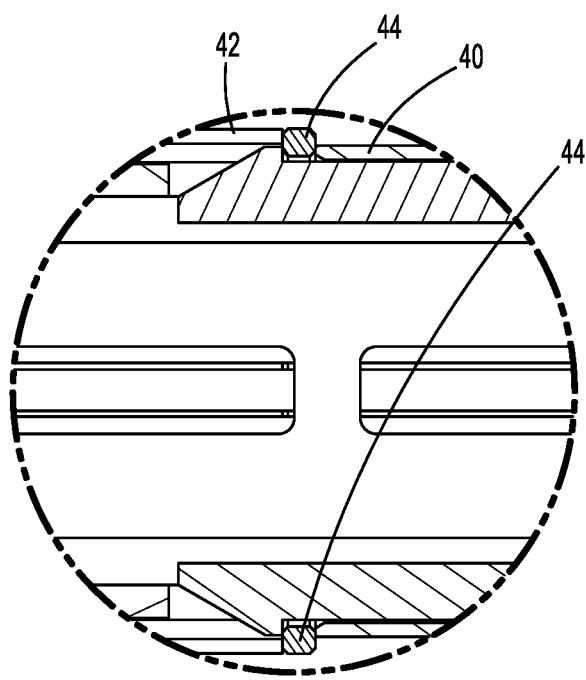

With reference now to FIGS. 6 and 6a, the body portion 18 (FIG. 4) of the loading unit 16 includes a seal member 44 positioned about the second portion 40 adjacent the third portion 42. The seal member 44 may be flush with the third portion 42. In embodiments, the seal member 44 may include an outer diameter that is smaller than an outer diameter of the third portion 42. Alternatively, the seal member 44 may include an outer diameter that is larger than an outer diameter of the third portion 42 such that the seal member 44 is interposed between the third portion 42 and the elongate member 14. The seal member 44 may be formed of an elastic or a compressible material to form a fluid-tight seal against an inner surface of the elongate member 14. The seal member 44 may be formed of, e.g., plastic, polymer, rubber, gel, or any combination thereof that can provide a fluid-tight seal between the loading unit 16 and the elongate member 14. Furthermore, the seal member 44 provides additional frictional contact with the elongate member 14, which, in turn, enhances securement of the loading unit 16 to the elongate member 14.

With reference now to FIGS. 7-9, the tubular member 56 of the elongate member 14 surrounds an actuation rod 58. The actuation rod 58 is configured to operatively couple the loading unit 16 (FIG. 4) with the actuation trigger 28 (FIG. 1) of the handle assembly 12. The tubular member 56 includes a coupling portion 49 that is dimensioned to receive the first and second portions 38, 40 (FIG. 5) of the body portion 18 of the loading unit 16.

The elongate member 14 includes a receiving portion 48 that is positioned within the tubular member 56 and is configured to be coupled with the loading unit 16. The receiving portion 48 is dimensioned to receive the actuation rod 58. The actuation rod 58 may extend partially into the coupling portion 49 to be operatively coupled with the loading unit 16. The coupling portion 49 has a first length "D" and the receiving portion 48 has a second length "R" that is smaller than the first length "D". For example, the first length "D" may be greater than twice the length of the second length "R".

With particular reference now to FIG. 8, the tubular member 56 may include a uniform diameter. An inner diameter of the tubular member 56 may be larger than outer diameters of the first and second portions 38, 40 (FIG. 5) of the loading unit 16. An outer diameter of the tubular member 56 may be, e.g., approximately equal, to an outer diameter of the third portion 42 (FIG. 5) of the loading unit 16. Under such a configuration, the tubular member 56 will extend over the first and second portions 38, 40 of the loading unit 16 when the loading unit 16 is coupled to the elongate member 14 to increase the rigidity of the loading unit 16 and stabilize the position of the tool assembly in relation to the elongate member 14. Such a configuration further enhances the connection between the loading unit 16 and the elongate member 14 by enclosing a substantial portion of the loading unit 16, i.e., enclosing the first and second lengths "A", "B" (FIG. 5) of the first and second portion 38, 40, within the tubular member 56 of the elongate member 14.

In operation, after layers of tissue are positioned between tissue contacting surfaces of the cartridge assembly 22 and the anvil assembly 24, the handle assembly 12 is actuated for sequentially ejecting surgical staples through respective staple retention slots, whereby interaction between surgical staples and the anvil assembly 24 deforms the surgical staples through the layers of tissue to join the layers of tissue. Reference may be made to the '943 Patent and also to U.S. Pat. No. 6,202,914, the entire contents of which are also incorporated herein by reference, for a detailed discussion of the construction and operation of the handle assembly 12 and the tool assembly 20 during staple firing and staple formation.

With reference to FIGS. 10 and 10a, the surgical stapling device 10 may be used with an access port 60 including a housing 61 having a fluid port 64 and a port seal 62 that provides a fluid-tight seal about an object that is inserted through a lumen 63 defined in the housing 61. The fluid port 64 may be, e.g., an insufflation port, coupled to a fluid supply (not shown). As discussed hereinabove, the coupling portion 49 of the tubular member 56 (FIG. 7) of the elongate member 14 has a length to receive the first and second portions 38, 40 of the loading unit 16 (FIG. 5). Under such a configuration, the seal member 44 of the loading unit 16 is positioned distal of the port seal 62 of the access port 60, when the loading unit 16 is received through the access port 60. Such a configuration may maintain the sterilization of the access port 60 and the surgical stapling device 10.

Figure 11:
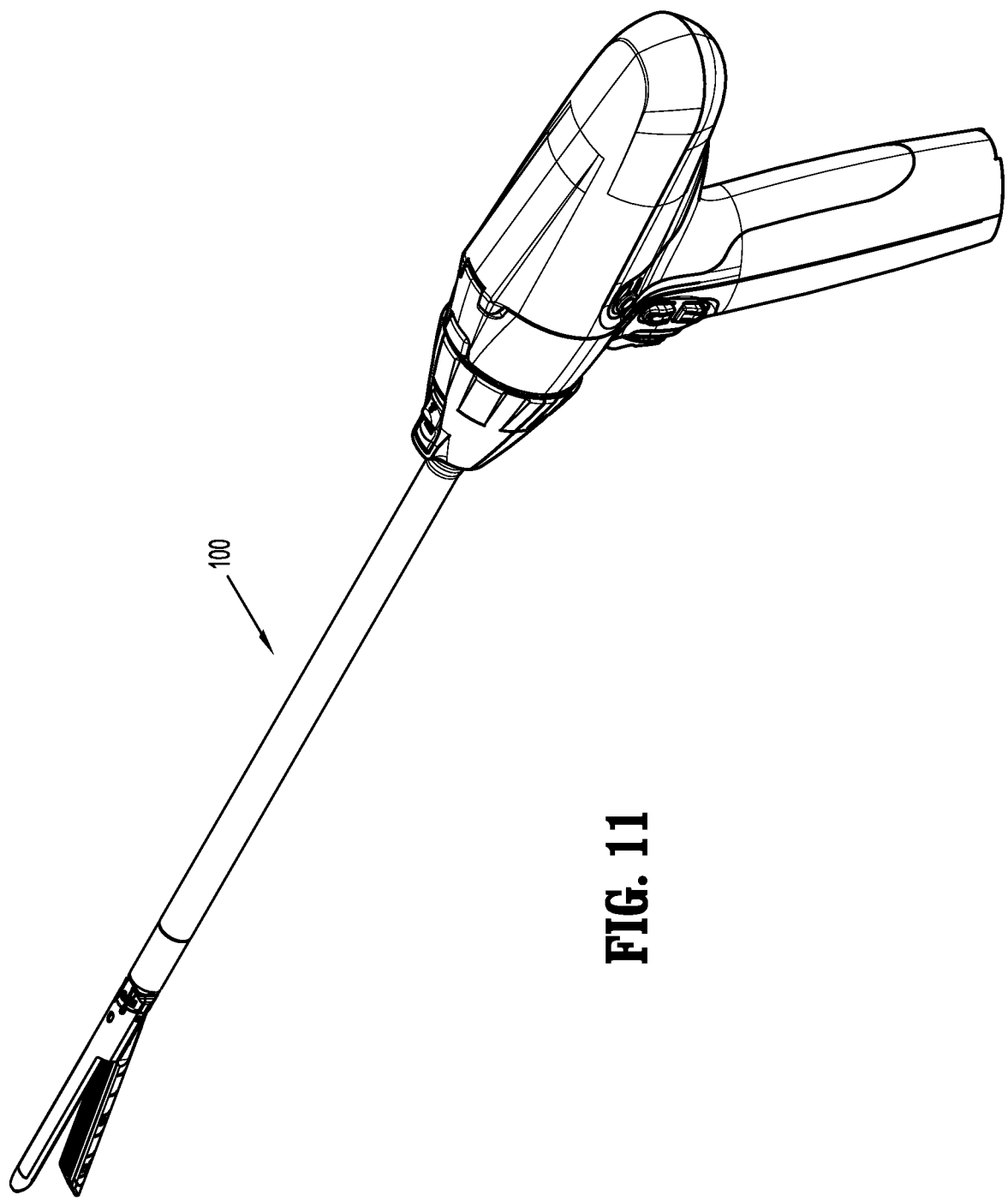
FIG. 11 is a perspective view of a powered surgical stapling device including the loading unit of FIG. 1.

Persons skilled in the art will understand that the structures and methods specifically described herein and shown in the accompanying figures are non-limiting exemplary embodiments, and that the description, disclosure, and figures should be construed merely as exemplary of particular embodiments. For example, it is further contemplated that the elongate member 14 and the loading unit 16 may be incorporated into a number of surgical devices, such as, e.g., a powered surgical stapling device 100 (FIG. 11). It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed:

1. A surgical stapling device comprising:
an elongate member defining a lumen therethrough; and
a loading unit releasably attachable to the elongate member, the loading unit including a tool portion and a body portion configured to be releasably coupled to the elongate member, the body portion including:
a first portion having a first length, the first portion configured to be releasably secured with the elongate member;
a second portion having a second length, the second portion being positioned distally of the first portion and dimensioned to be received within the elongate member;
a seal member disposed about the second portion; and
a third portion having a third length, the third portion being positioned distally of the second portion, at least the second or third portion configured to engage the elongate member in a sealing relation, wherein the second length is greater than the first and third lengths.

2. The surgical stapling device according to claim 1, wherein the third portion of the body portion is dimensioned to be flush with the elongate member when the first and second portions are received in the elongate member.

3. The surgical stapling device according to claim 1, wherein the second length of the second portion is greater than the sum of the first and third lengths.

4. The surgical stapling device according to claim 1, wherein the second portion of the body portion is dimensioned to provide a frictional contact with the elongate member.

5. The surgical stapling device according to claim 1, wherein the second portion of the body portion has a second diameter and the third portion has a third diameter larger than the second diameter.

6. The surgical stapling device according to claim 1, wherein the second portion of the body portion has a uniform diameter.

7. The surgical stapling device according to claim 1, wherein the seal member is disposed adjacent the third portion.

8. The surgical stapling device according to claim 1, wherein the seal member may be flush with the third portion.

9. The surgical stapling device according to claim 1, wherein the seal member has a diameter larger than a diameter of the third portion.

10. The surgical stapling device according to claim 1, wherein the seal member is formed of elastic or compressible material to form a fluid-tight seal against an inner surface of the elongate member.

11. The surgical stapling device according to claim 1, wherein the elongate member has a uniform diameter.

12. A surgical kit comprising:
a surgical stapling device including:
an elongate member defining a lumen therethrough; and
a loading unit releasably attachable to the elongate member, the loading unit including:
a tool portion including an anvil assembly and a cartridge assembly; and
a body portion configured to be releasably coupled to the elongate member, the body portion including:
a first portion having a first length, the first portion configured to be releasably secured with the elongate member;
a second portion having a second length, the second portion distal of the first portion, the second portion dimensioned to be received in the elongate member, the second portion including a seal member configured to provide a fluid-tight seal against the elongate member; and
a third portion having a third length, the third portion distal of the second portion, the third portion configured to engage the elongate member in a sealing relation; and
an access port including:
a housing including a lumen dimensioned to receive the loading unit and the elongate member of the surgical stapling device, the housing including a fluid port and a seal disposed in the lumen to provide a fluid-tight seal against an object inserted therethrough; and
a tubular member extending from the housing, wherein the second portion of the body portion of the surgical stapling device is disposed distal of the seal of the access port when the elongate member and the loading unit are received through the access port.

13. The kit according to claim 12, wherein the second length of the second portion of the surgical stapling device is greater than the first and third lengths of the first and third portions of the surgical stapling device.

14. The kit according to claim 13, wherein the second length is greater than the sum of the first and third lengths.

15. The kit according to claim 12, wherein the third portion of the surgical stapling device is dimensioned to be flush with the elongate member of the surgical stapling device when the first and second portions of the surgical stapling device are received in the elongate member.

16. The kit according to claim 12, wherein the second portion of the surgical stapling device is dimensioned to provide a frictional contact with the elongate member of the surgical stapling device.

17. The kit according to claim 16, wherein the second portion of the surgical stapling device has a second diameter and the third portion of the surgical stapling device has a third diameter larger than the second diameter.

18. A surgical stapling device comprising:
an elongate member defining a lumen therethrough; and
a loading unit releasably attachable to the elongate member, the loading unit including a tool portion and a body portion configured to be releasably coupled to the elongate member, the body portion including:
a first portion having a first length;
a second portion having a second length, the second portion being positioned distally of the first portion and configured to be received within the elongate member to provide rigidity to the elongate member;
a third portion having a third length, the third portion being positioned distally of the second portion; and
a seal member disposed adjacent the third portion to form a seal against the elongate member,
wherein the second length is greater than the first and third lengths combined.

19. The surgical stapling device according to claim 18, wherein the seal member may be flush with the third portion.

* * * * *